United States Patent [19]

Glassman

[11] Patent Number: 5,140,997
[45] Date of Patent: Aug. 25, 1992

[54] OPHTHALMOLOGIC SURGICAL DRAPE WITH BREATHING MEANS

[76] Inventor: Jacob A. Glassman, 1680 Michigan Ave., Miami Beach, Fla. 33139

[21] Appl. No.: 416,863

[22] Filed: Oct. 4, 1989

[51] Int. Cl.$^5$ .................. A61B 19/00; A61F 11/00
[52] U.S. Cl. ........................... 128/849; 128/857
[58] Field of Search .............. 128/847, 849–857

[56] References Cited

U.S. PATENT DOCUMENTS

| | | | |
|---|---|---|---|
| 1,475,105 | 11/1923 | Aasen | 128/863 |
| 1,582,164 | 4/1926 | Burstyn | 128/863 |
| 3,315,672 | 4/1967 | Cunningham | 128/863 |
| 3,438,370 | 4/1969 | Krantz, Jr. | 128/863 |
| 3,625,207 | 12/1971 | Agnew | 128/847 |
| 3,747,599 | 7/1973 | Malmin | 128/847 |
| 3,878,843 | 4/1975 | Morgan | 128/851 |
| 3,955,570 | 5/1976 | Hutter | 128/863 |
| 3,990,112 | 11/1976 | Ciffolillo | 128/863 |
| 4,821,340 | 4/1989 | Johnson | 128/863 |

FOREIGN PATENT DOCUMENTS 0556664  12/1974  Switzerland .................. 128/863

Primary Examiner—Robert A. Hafer
Assistant Examiner—Michael Brown
Attorney, Agent, or Firm—Richard M. Saccocio

[57] ABSTRACT

An improved ophthalmological drape having breathing devices associated therewith is disclosed. A nozzle tube is permanently attached to the location of a patient's nostrils relative to the his eyes, such that when the drape is fitted to the eye to be operated upon, the nozzle tube which delivers oxygen to the patient is substantially located underneath the patient's nostrils. A breathing surgical filtering mask is incorporated within the surgical drape directly below the oxygen supply nozzle device so as to provide an adequate respiratory exchange and an escape of the patient's expired air with carbon dioxide from his lungs.

10 Claims, 2 Drawing Sheets

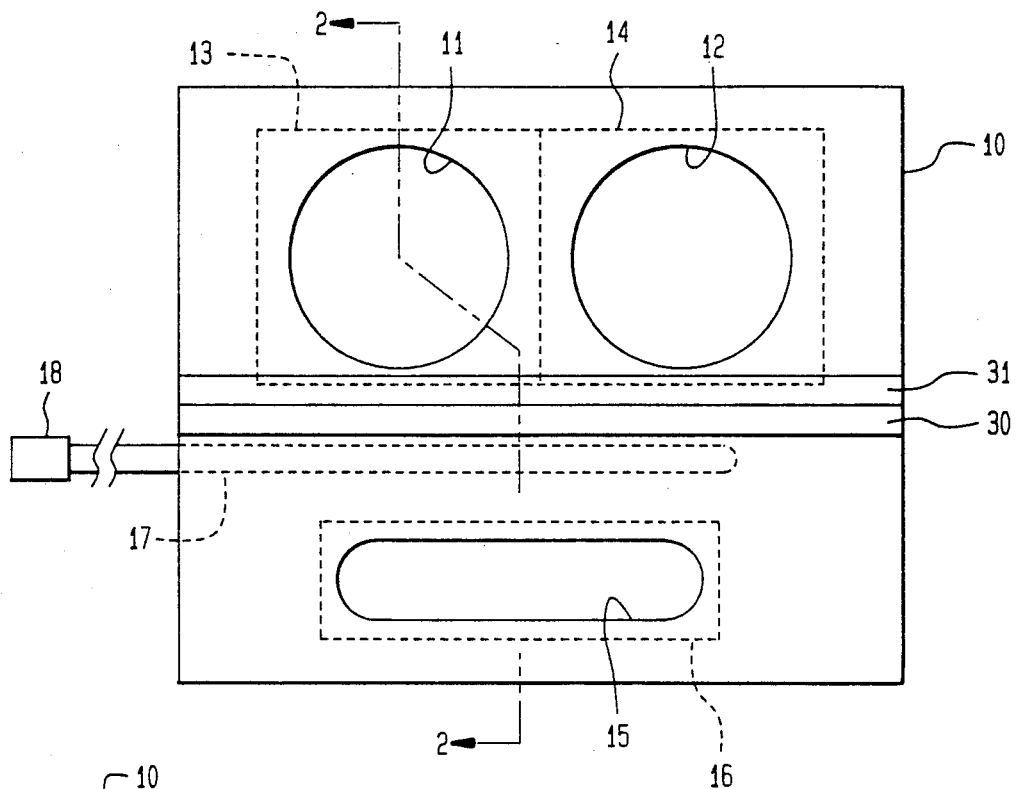
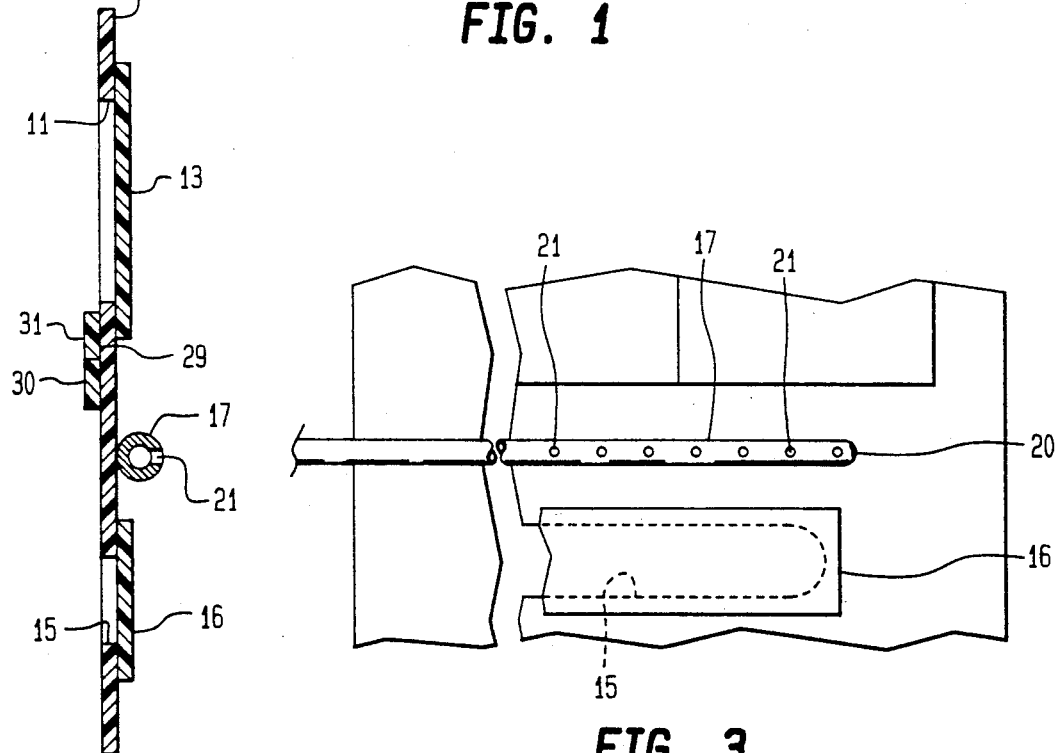
FIG. 1
FIG. 2
FIG. 3

OPHTHALMOLOGIC SURGICAL DRAPE WITH BREATHING MEANS

CROSS REFERENCE TO RELATED APPLICATION

This application is related to my U.S. patent application Ser. No. 07/387,419, filed Jul. 31, 1989, and entitled "Ophthalmic Drape with Built-In Mini-Mask," by Jacob A. Glassman, M.D., which comprises a continuation-in-part of U.S. patent application Ser. No. 07/295,644, filed Jan. 3, 1989, now abandoned.

BACKGROUND OF THE INVENTION

1. Field of the Invention

This invention relates in general to the field of ophthalmological surgical drapes and in particular to apparatus for draping the head and/or head and body of a patient who is undergoing ophthalmological surgery, including means for delivering oxygen to the nose and mouth of the patient.

2. Description of the Prior Art

For surgical operations on the eyes, such as removing cataracts, the patient's face is covered with a drape which usually comprises a sheet or film of plastic material having an opening therethrough in the area of the location of the eye site surgery. When first applied, the drape rests lightly over the mouth and nose of the patient, while the area around the operated eye is glued to the drape. As the surgery progresses, the drape tends to adapt itself more snugly against the nose, mouth, and eye area of the patient due to a variety of factors. One such factor is the natural tendency of the film or plastic to flatten and contour itself about the shape of the patient's face and head. Other factors include the weight of instruments and/or the hands of the nurse or surgical assistant which may inadvertently distort and move the drape about the patient's nose and mouth. This can lead to the unfortunate asphyxiation of a patient who is well covered and over sedated and cannot complain. A patient who is not well sedated will struggle for air and otherwise thrash about in order to improve his or her breathing. Undue body motion can be very detrimental to the surgical procedure. In the latter circumstance, the operating surgeon usually requests more sedation to quiet the patient; however, this leads to a well sedated patient with a further possibility of asphyxiation. Accordingly, sedated patients must be carefully and continuously monitored by an attending anesthesiologist to make sure the patient is still breathing adequately and safely. However, this leads to a well sedated patient with a further possibility of asphyxiation. Accordingly, sedated patients must be carefully and continuously monitored by an attending anesthesiologist to make sure the patient is still breathing adequately and safely.

In order to overcome any of the breathing problems associated with the prior art, a majority of ophthalmologists employ direct intranasal tubing with two long tube extensions that are inserted into each of the patient's nostrils and which supply a constant direct flow of measured oxygen into the patient's nasal canal. These ophthalmologists may also employ an additional tubing apparatus placed below the chin level to draw off the air, which includes carbon dioxide, $CO_2$, exhaled by the patient which is known to accumulate under the drape. The surgeons who draw off the patient's exhaled air are primarily concerned that the accumulated carbon dioxide content in the exhaled air may give rise to acidosis and possible undesirable hypertension. Where no separate apparatus is used to draw off the accumulated exhaled air containing carbon dioxide, some surgeons will allow the four sides of the plastic facial drape to remain loose so that the exhaled air can readily escape. This latter technique may not always be effective.

With the intranasal oxygen supply apparatus, a continuous flow of oxygen is directly fed to the patient via a fine plastic catheter that has two cannulae extensions, each of which enter deeply into each nostril. The intranasal catheter is held in place by two bands encircled around the ear lobes of the patient. The two intranasal cannulae are further secured to the side of the face with two strips of adhesive tape. Following fixation of the intranasal breathing apparatus to the patient, the draping of the non-surgical portions of the body is then effectuated. It is well known that certain patients do not tolerate the intranasal breathing apparatus. It can cause them to become nervous and irritable, which in turn makes them squirm or thrash about uncontrollably, which movements can seriously interfere with the effectiveness and progress of the surgery. In such instances, the stand-by anesthesiologist administers more intravenous (I.V.) sedation to the patient until all undue movements subside. This has, on certain occasions, resulted in an over sedated patient who then may give no warning sign that the intranasal breathing apparatus has slipped out of the nose, or became disconnected, kinked, or plugged, thereby causing breathing difficulties and even possible unrecognized asphyxiation.

The disadvantages of the intranasal breathing apparatus may be listed in the order of their seriousness as follows: 1) intolerance, and irritation to the nasal mucosa with marked discomfort, 2) the possibility of the small two cannulae extensions of the intranasal apparatus slipping out of one or both nostrils, and thereby subjecting the patient to a silent and unrecognized anoxia, and possible asphyxia, and 3) may induce possible restlessness, irritability, and even arrythmia, all of which may lead to serious cardiac consequences to an aged patient.

In U.S. Pat. No. 4,739,753, by Vrehm, issued Apr. 26, 1988, entitled "Surgical Drape Support and Oxygen Delivery System," the inventor discloses a tubing arrangement which is disclosed and which supplies oxygen to a patient undergoing surgery. An oxygen supply is connected to one end of the tubing while a nozzle is attached to the other end of the tubing in the vicinity of the patient's nose. This invention is a body drape with tubing built in and made relatively stiff to support the weight of the nozzle at the end thereof, as the drape lies over the patient. Thus, the area of the nose of the patient is free of the drape and yet receives a supply of oxygen. In this apparatus, no provision is made for withdrawal of the exhaled carbon dioxide from the patient. Another disadvantage of this apparatus comprises the bulkiness and absence of accuracy of the apparatus which can in addition physically interfere with the critical movements of the operating surgeon; yet another disadvantage is the expense associated with such an apparatus, especially if it is disposable. Most important, it is not an ophthalmological drape.

Accordingly, the main objective of my new ophthalmological drape is to supply oxygen to a patient by indirect means, that is, not as unwieldy and cumbersome as the two canaliculae placed directly into the nostrils of a patient, and yet will assure an adequate, safe, and controlled delivery of oxygen to the patient throughout the surgery.

Another object of my present invention is to provide an ophthalmological drape which provides a surgical mini-mask for escape of carbon dioxide in the expired air of the patient while being completely covered under the surgical drape.

Another object of my present invention is to provide an ophthalmological drape which is proportioned and provided with means to allow the drape to be used by a multitude of different patients having variable sized and contoured faces (long and transverse) and with variable distances between eyes, nose and mouth.

The above-stated objects as well as other objects which, although not specifically stated, but are intended to be included within the scope of the present invention, are accomplished by the present invention and will become apparent from the hereinafter set forth Detailed Description of the Invention, Drawings, and the Claims appended herewith.

SUMMARY OF THE INVENTION

The present invention accomplishes the above-stated objectives as well as others, by providing an ophthalmological surgical drape which indirectly supplies oxygen both nostrils and mouth area of a patient undergoing eye surgery. The present inventive surgical drape further includes means for escape of the undesirable carbon dioxide-rich expired air exhaled by the patient. Further, the inventive surgical drape allows for surgery to either one or both of the patient's eyes, while providing for the oxygen supply and the respiratory exchange of the expired air. Also, the surgical drape is adjustable so that one surgical drape may be used effectively fitted to a variable number of different sized faces and heads.

A plastic film, such as that commonly used for ophthalmological drapes, is provided with one or two apertures which are individually and adhesively covered by another non-adhesive film of plastic. Another aperture is provided directly below the eye apertures, which is covered by a filtering material similar to that used in a surgical mask so that the expired air of the patient may be directed therethrough and discharged into the room atmosphere. In one embodiment, a small diameter plastic tube is permanently fixed to the underside of the facial drape, just above the aperture for expiratory exchange. An oxygen supply is delivered via this small diameter flexible tubing and is directed under the drape to the nose and mouth area of a patient. The small diameter flexible tubing has a plurality of small openings through the wall thereof which serve as nozzles directing the flow of oxygen to both the patient's nostrils and mouth. At least one transverse covered strip of adhesive is provided with the inventive ophthalmological drape below the eye apertures and above the mouth aperture for purposes of permitting the drape to be transversely folded to shorten or lengthen the distance between the eye apertures and the mouth aperture and thereby allowing the fit of the drape to be individualized and ideally fitted to the particular patient being operated upon.

BRIEF DESCRIPTION OF THE DRAWINGS

Various other objects, advantages, and features of the invention will become apparent to those skilled in the art from the following discussion taken in conjunction with the following drawings, in which:

FIG. 1 is a top plan view of my new ophthalmological drape illustrating the various features thereof;

FIG. 2 is a cross-sectional view taken through the line 2—2 of FIG. 1;

FIG. 3 is an bottom plan view of a portion of the drape showing the nozzle tube which is permanently attached to the underside of the inventive drape just above the mini mask;

DESCRIPTION OF THE PREFERRED EMBODIMENTS

Figure 4:
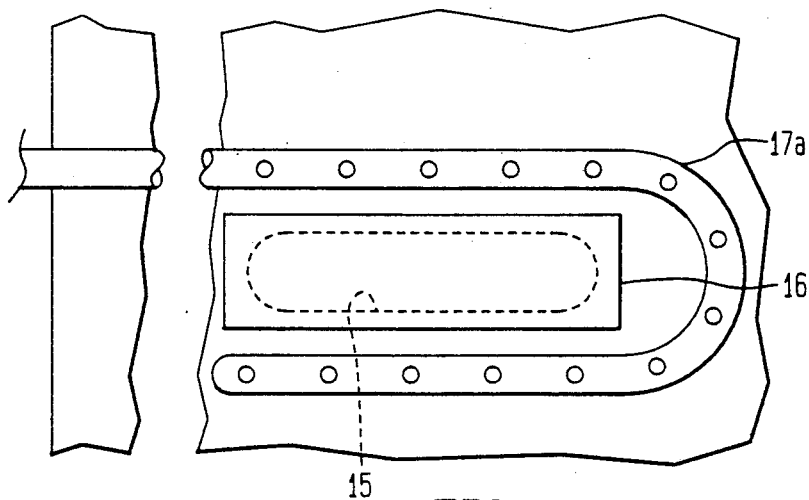
FIG. 4 is another embodiment of the nozzle means used to direct oxygen to the nostrils and mouth area of a patient.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various figures are designated by the same reference numerals.

Reference is now made to FIGS. 1 through 6 of the drawings, which taken together, illustrate the various features of the inventive ophthalmological drape 10. The material from which the drape 10 is manufactured comprises a thin sheet or film of transparent plastic such as that which is generally used for surgical eye procedures. Either one or a pair of side-by-side circular apertures 11 and 12 allow the ophthalmological drape to be used for either a left- or a right-eye operation or, for a left and a right eye operation. Each of the apertures 11 and 12 are individually covered by a sheet of non-adhesive plastic 13 and 14, respectively, either one of which may be individually removed by simply peeling it from the adhesive back of the ophthalmological drape 10 and thereby expose the selected eye-opening aperture 11 or 12 whichever is desired to be utilized for the particular surgery to be conducted. As in the past, the underside of the ophthalmological drape 10 lying under the protective coverings 13 and 14, which may or may not be provided with a thin film of adhesive, which when covering 13 or 14 is removed, the selected aperture 11 or 12 is exposed and allows for the drape to be adhesively secured to the area around the eye being operated upon.

Below the eye apertures 11 and 12, lies another aperture 15 having a generally rectangular or oval configuration. Aperture 15 is provided and located such that it is positioned near to the nostrils and directly over the mouth of the patient almost simultaneously as the surgical drape 10 is fitted to the peri-periphery of the particular eye exposed for the surgery. Aperture 15 is covered with a specific filter fabric or fiber mesh material 16 that permits easy respirations (inhalations and exhalations), as it filters bacteria, fluids, and other particulate matter from the expired air of the patient.

The air filtering surgical mask 16 may be made of a material extensively used in regular surgical masks and is further explained in my co-pending U.S. patent application Ser. No. 07/387,419, filed Jul. 31, 1989, and entitled "Drape with Built-In Mini-Mask," which comprises a continuation-in-part of U.S. patent application Ser. No. 07/295,644, filed Jan. 3, 1989, now abandoned, the contents of which are incorporated herein by reference.

A nozzle tube comprising an elongated length of small diameter tubing 17, which may be flexible, is permanently attached to the underside of the plastic material of the drape just above mask 16. The tubing 17 extends transversely under the drape 10 and extends out from a side thereof away from the face of the patient so that when it is connected to an oxygen source, the making of the connection will not disturb the carefully placed surgical drape 10 and mask 15. One end 20 of nozzle tube 17 is closed while the other end includes a connector half 18 so as to readily accept the insertion therein of a mating connector half attached to standard tubing generally utilized with oxygen breathing apparatus. Nozzle tube 17 includes a plurality of small openings 21 provided through the wall of the tube 17 extending from the inner circumference thereof radially outward specifically in the direction of the location of a patient's mouth and nostrils, which patient is covered with the ophthalmological drape 10. The connector end 18 of tubing 17 may be conventionally attached to a source of oxygen for purposes of supplying the same to nozzle tube 17. A plan view of the nozzle tube 17 at the location of the breathing aperture 15 is shown in FIG. 3 of the drawings.

Another embodiment of the nozzle tube 17A is shown in FIG. 4 of the drawings. In this embodiment, the tubing 17A extends around the upper and lower side of the filtering aperture 15 so as to supply oxygen to the nostril area and the mouth area of the patient. A complete circular nozzle may also be utilized.

Figure 5:
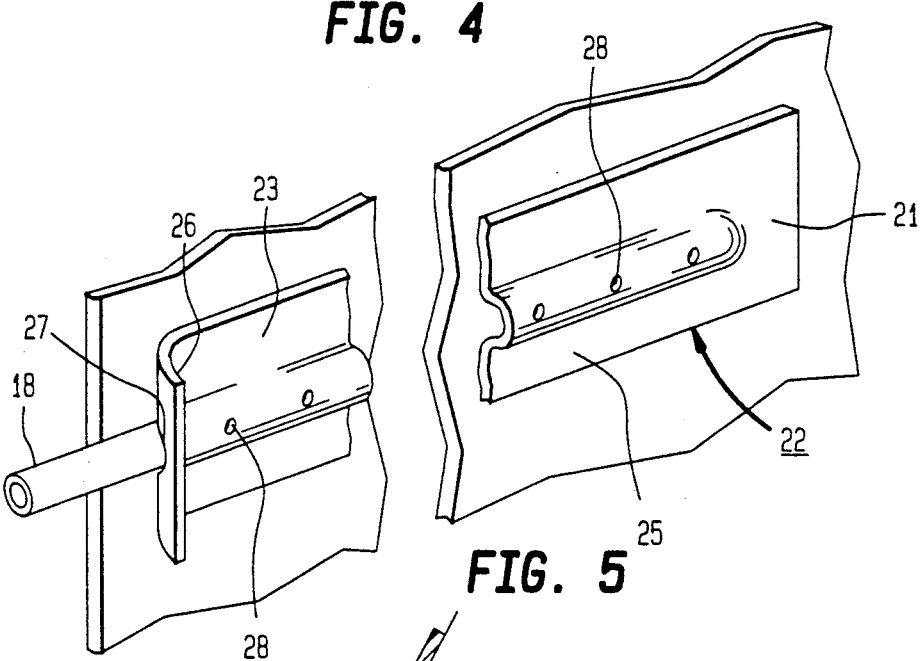
FIG. 5 is another embodiment of the nozzle means.

Yet another embodiment of the nozzle tube is shown in FIG. 5 of the drawings. In this embodiment, the nozzle tube 22 comprises an elongated strip of plastic (such as that used for the ophthalmological drape 10) which is secured along three edges 23, 24, and 25 thereof to the body of the ophthalmological drape 10. Simple heat bonding may be utilized to secure the three sides 23, 24, and 25 of the nozzle tube 22 to ophthalmological drape 10. The remaining side 26 of nozzle tube 23 is left unattached to the drape 10 such that it may be lifted away from the surface of the drape 10, thereby exposing a central opening 27 of the nozzle tube 23 at the side edge of drape 10. A locking connector half 18 is attached to the open end 27 of nozzle 23 so that a mating connector half attached to the oxygen supply may be lock connected to connector half 18. A plurality of holes 28 may be provided along the length of the center unattached portion of the strip of plastic comprising the nozzle tube 22 of this embodiment. Holes 28, of course, direct the oxygen flow to the nostril and mouth areas of the patient being surgically operated upon. Nozzle 22 may, as in the embodiment of FIG. 4, extend around mask-filtering aperture 15 so as to supply oxygen to both the nostrils and mouth of the patient.

Figure 6A:
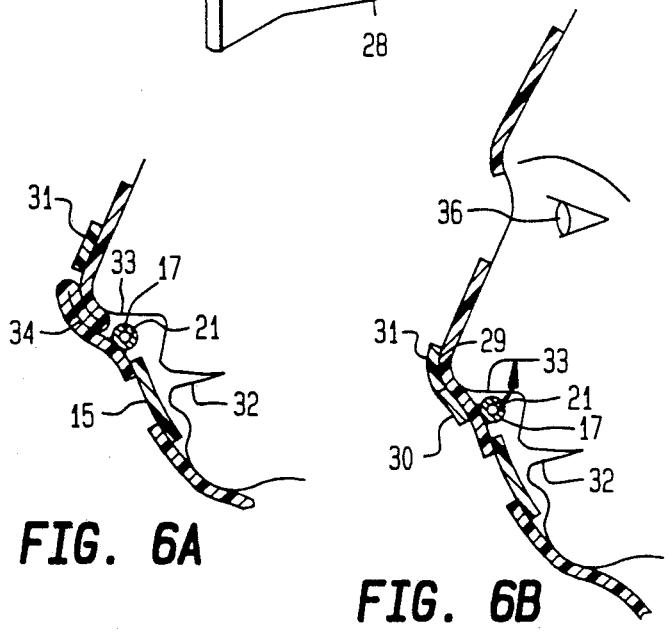
FIG. 6A–6C schematically illustrates the side profile of a patient with the face being covered by the inventive ophthalmological drape.
Figure 6B:
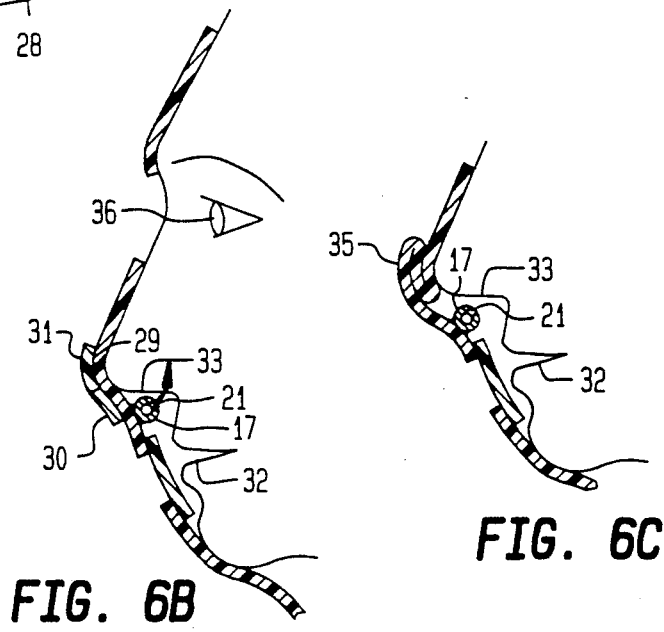
Figure 6C:
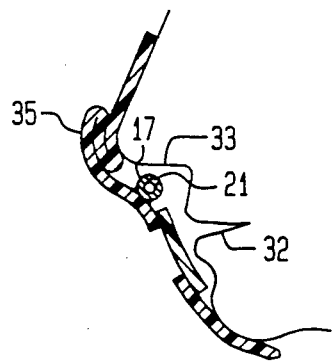

FIG. 6 schematically illustrates the side profile view of a patient being covered with the inventive ophthalmological drape 10. The lengthwise adjustability of ophthalmological drape 10 is clearly shown in FIG. 6. The lengthwise adjustability of ophthalmological drape 10 comprises a film of adhesive 29 extending transversely across the width of the drape 10 above the level of nozzle tube 17 and below the eye apertures 11 and 12 (as seen in FIG. 1). The eye selected to be operated upon is covered by either aperture 11 or 12, as appropriate, and secured thereto by the adhesive surface thereunder. The location of the filtering aperture 15 and the nozzle tube 17 relative to the patient's mouth 32 and nostrils 33 are then checked. If the fitup is proper as shown in FIG. 6A, no lengthwise adjustment is made to drape 10. It is to be noted that the drape 10 may initially be furnished with a lengthwise fold 34 as shown in FIG. 6A so that the drape 10 may be adjusted upwardly or downwardly to adjust the oxygen carrying nozzle tube 17 to the underside of the patient's nostrils. However, should the nozzle tube 17 and the surgical mask 15 be too far below the patient's nostrils 33 and mouth 32, then plastic covering strip 31 may be removed and the ophthalmological drape 10 may be folded further upwardly 35 as shown in FIG. 6C.

Assuming further that when the drape 10 is first fitted to the patient, the nozzle tube 17 and the surgical mask 15 are too far above the patient's nostrils 33 and mouth 32, then the drape 10 must be lengthened as shown in FIG. 6B.

Here, the ophthalmological drape 10 has been increased in length by unfolding fold 34. A film covering strip 30 may then be placed over that portion of film 29 which was uncovered when fold 34 was undone. During adjustment of the location of the nozzle means 17 and mask portion 15 relative to the nostril openings 33 and mouth 32 of the patient, it is necessary that the fitup of the drape 10 relative to the patient's selected eye 36 be properly fixed and so maintained. In this manner, the inventive drape 10 may be adjusted lengthwise in order to position eye apertures 11 or 12, the nozzle tube 17 and the surgical mask 15 in their proper positions relative to the patient's eye, nostrils and mouth. Thus, every patient's face is fitted individually and correctly.

While the invention has been described, disclosed, illustrated and shown in certain terms or certain embodiments or modifications which it has assumed in practice, the scope of the invention is not intended to be nor should it be deemed to be limited thereby and such other modifications or embodiments as may be suggested by the teachings herein are particularly reserved especially as they fall within the scope of the breadth and scope of the claims here appended.

I claim as my invention:

1. An ophthalmological surgical drape adapted for supplying oxygen to a patient, venting of exhaled air and for exposing one or both of a patient's eyes while covering his nostril openings and his mouth, comprising a thin sheet of plastic having one or more eye apertures, said thin sheet of plastic having a flexibility so as to adapt itself up against facial features of said patient, filtering aperture means for covering said patient's mouth and allowing exhaled air to be vented, and nozzle means for supplying oxygen to the nostril openings of said patient.

2. The surgical drape of claim 1, wherein said filtering aperture means comprises an elongated opening in said drape, said opening being covered by a surgical mask filtering material.

3. The surgical drape of claim 1, wherein said nozzle means comprises a tube having one end closed and one end open with a plurality of holes through the wall of said tube extending along the length thereof.

4. The surgical drape of claim 3, wherein said nozzle means commences at the location of said filtering apparatus means and extends across the width of said drape, terminating at said open end which extends beyond one side edge of said drape, said nozzle means being located between said one or more eye apertures and said filtering aperture means.

5. The surgical drape of claim 4, wherein said nozzle tube extends around said filtering aperture means.

6. The surgical drape of claim 1, wherein said nozzle means supplies oxygen to the nostril openings and the mouth of said patient.

7. The surgical drape of claim 3, wherein said tube comprises an elongated thin ribbon of plastic heat sealed around three sides thereof to said plastic sheet of said surgical drape.

8. The surgical drape of claim 1, comprising adjustable means for adjusting the length of said drape to individually fit the eye, the nose, and the mouth of said patient.

9. The surgical drape of claim 8, wherein said adjustable means comprises a film of adhesive extending along the width of said drape between said one or more eye apertures and said nozzle means whereby said drape may be folded over and adhesively joined together at said fold, thereby lengthening or shortening the distance between the eye apertures and the nozzle tube.

10. The surgical drape of claim 9, wherein said film of adhesive is covered by a protective film of plastic sheeting.

* * * * *